(12) United States Patent
Pageon

(10) Patent No.: US 7,005,148 B2
(45) Date of Patent: Feb. 28, 2006

(54) USE OF AN EXTRACT OF AT LEAST ONE VACCINIUM-TYPE PLANT AS AN ANTI-GLYCATION AGENT

(75) Inventor: Hervé Pageon, Puteaux (FR)

(73) Assignee: L'Oreal, Paris (FR)

( * ) Notice: Subject to any disclaimer, the term of this patent is extended or adjusted under 35 U.S.C. 154(b) by 44 days.

(21) Appl. No.: 10/168,309

(22) PCT Filed: Dec. 14, 2000

(86) PCT No.: PCT/FR00/03530

§ 371 (c)(1),
(2), (4) Date: Sep. 27, 2002

(87) PCT Pub. No.: WO01/45648

PCT Pub. Date: Jun. 28, 2001

(65) Prior Publication Data
US 2003/0138393 A1    Jul. 24, 2003

(30) Foreign Application Priority Data
Dec. 21, 1999  (FR) .................................. 99 16166

(51) Int. Cl.
*A61K 35/78* (2006.01)
(52) U.S. Cl. ...................................... 424/732; 424/401
(58) Field of Classification Search ................ 424/401, 424/732
See application file for complete search history.

(56) References Cited

U.S. PATENT DOCUMENTS 5,384,123 A    1/1995   Metsada

FOREIGN PATENT DOCUMENTS

| EP | 0 914 816 | 5/1999 |
|----|-----------|--------|
| FR | 2 612 775 | 9/1988 |
| FR | 2 663 848 | 1/1992 |
| FR | 2 736 263 | 1/1997 |
| FR | 2 774 366 | 8/1997 |
| GB | 2 159 053 | 11/1985 |
| WO | WO 98/05294 A1 * | 2/1998 |
| WO | WO 98/51291 | 11/1998 |

OTHER PUBLICATIONS

CAPLUS English abstract of FR 2 612 775 (1988).*
www.botany.com/vaccinium.html.*
Database CAPLUS, Chemical Abstracts Service, Columbus, Ohio; Database accession No. 2000:658029, XP002167156, Abstract and JP 2000 256176 A (Shalome KK), Jun. 6, 2000.

* cited by examiner

*Primary Examiner*—Susan D. Coe
(74) *Attorney, Agent, or Firm*—Buchanan Ingersoll, P.C.

(57) ABSTRACT

The invention relates to the use of at least one extract of at least one *Vaccinium*-type plant as the active agent in a composition or for producing a composition, in a physiologically suitable medium, said extract or said composition being intended to reduce or even inhibit the glycation of proteins, especially proteins of the skin or associated structures.

16 Claims, No Drawings

USE OF AN EXTRACT OF AT LEAST ONE VACCINIUM-TYPE PLANT AS AN ANTI-GLYCATION AGENT

The present invention relates to the use, as active ingredient, in a physiologically acceptable medium, of at least one extract of at least one plant of the genus *Vaccinium* in a composition or for the preparation of a composition, the extract or the composition being intended for reducing or even inhibiting glycation of proteins, particularly proteins of the skin and/or of its annexes.

Glycation is a nonenzymatic process involving a monosaccharide (glucose or ribose) which reacts according to the Maillard reaction with an amino group of an amino acid residue (such as for example lysine), particularly an amino acid residue of a protein, to form a Schiff base. The latter, after a molecular rearrangement called Amadori rearrangement, may lead, through a succession of reactions, to bridging, particularly intramolecular bridging such as for example of the pentosidine type.

This phenomenon increases regularly with age. It is characterized by the appearance of glycation products whose content increases regularly with age. The glycation products are for example pyrraline, carboxymethyllysine, pentosidine, crossline, $N^\epsilon$(2–25 carboxyethyl)lysine (CEL), glyoxallysine dimer (GOLD), methylglyoxallysine dimer (MOLD), 3DG-ARG imidazolone, versperlysines A, B, C, threosidine or alternatively advanced glycosylation end-products or AGEs.

The glycation of proteins is therefore a universal phenomenon, well known for the skin, particularly for its dermal component, but which also occurs in the annexes thereof such as the nails or the hair, particularly on the keratins and marginally in any protein system if the conditions required for glycation exist.

The human skin consists of two compartments, namely a superficial compartment, the epidermis, and a deep compartment, the dermis.

The natural human epidermis is mainly composed of three types of cells which are the keratinocytes, which are in the great majority, the melanocytes and the Langerhans' cells. Each of these cell types contributes, through its specific functions, to the essential role played in the body by the skin.

The dermis provides the epidermis a solid support. It is also its feeder component. It consists mainly of fibroblasts and of an extracellular matrix which is itself composed of various extracellular proteins, among which are in particular collagen fibres, elastin and various glycoproteins. All these extracellular components are synthesized by the fibroblast. Also present in the dermis are leukocytes, mastocytes and tissue macrophages. Finally, the dermis contains blood vessels and nerve fibres.

The fibroblast, by virtue of its activity in the synthesis of the extracellular matrix proteins (proteoglycans, collagen fibres and other structural glycoproteins) is the principal player in the structural formation of the dermis.

Collagen fibres are responsible for the strength of the dermis. They are very resistant but sensitive to certain enzymes generally called collagenases. In the dermis, the collagen fibres consist of fibrils which are firmly attached to each other, thus forming more than ten types of different structures. The structure of the dermis is in great part due to the entanglement of the packed collagen fibres. The collagen fibres participate in the tonicity of the skin.

Collagen fibres are regularly renewed but this renewal decreases with age, which causes in particular thinning of the dermis. It is also accepted that extrinsic factors such as ultraviolet rays, tobacco and some treatments (retinoic acid and derivatives, glucocorticoids, vitamin D and derivatives for example) also have an effect on the skin and on its collagen level.

In the dermal component of the skin, glycation occurs mainly in the dermis, on the collagen fibres, according to the process described above. The glycation of collagen increases regularly with age, causing a regular increase in the content of glycation products in the skin.

Without wishing to introduce any theory of skin ageing, it should be noted that other modifications of collagen which may also be a consequence of glycation, such as a reduction in heat denaturation, an increase in the resistance to enzymatic digestion and an increase in intermolecular bridgings, have been able to be demonstrated during skin ageing (Tanaka S. et al., 1988, J. Mol. Biol., 203, 495–505; Takahashi M. et al., 1995, Analytical Biochemistry, 232, 158–162). Furthermore, modifications due to glycation of certain constituents of the basal membrane, such as collagen IV, laminin and fibronectin have been able to be demonstrated (Tarsio J F. et al.,1985, Diabetes, 34, 477–484; Tarsio J F. et al., 1988, Diabetes, 37 532–539; Sternberg M. et al., 1995, C.R. Soc. Biol., 189, 967–985).

Thus, it can be understood why during skin ageing the physicochemical properties of collagen are modified and it becomes more difficult to solubilize and more difficult to degrade.

Thus, one of the components of aged skin indeed appears to be glycated collagen.

It is very well known that the skin results from a close association between at least two compartments constituting it, namely the epidermis and the dermis. The interactions between the dermis and the epidermis are such that it is reasonable to think that a modification of one can have consequences on the other. It can be suspected that the ageing of the dermis in particular, with its glycation phenomena, is bound to have consequences on the epidermis which is associated with it. Thus, during skin ageing, the glycation of collagen should result in modifications of the epidermis which necessarily participate in the ageing of the epidermis.

Thus, if the glycation of the proteins of the dermis, particularly of collagen causes as many damaging consequences on the skin, similar consequences are to be expected of the glycation of proteins on the annexes of the skin, such as for example the nails and/or the hair and in fact on any protein system.

It is therefore possible to understand the importance of having products which reduce or even inhibit the phenomenon of glycation of proteins.

In this regard, the applicant has surprisingly and unexpectedly discovered that extracts of plants of the genus *Vaccinium* have the property of reducing or even inhibiting the phenomenon of glycation of proteins.

Plants of the genus *Vaccinium* belong to the Ericaceae family which comprises about one hundred genera.

In the prior art, extracts of plants of the Ericaceae family are used, inter alia, as antioxidants.

However, the capacity of extracts of plants of the genus *Vaccinium* to reduce or even inhibit the phenomena of glycation has never been described up until now.

The subject of the invention is therefore the use, in a composition or for the preparation of a composition, of an effective quantity of at least one extract of at least one plant of the genus *Vaccinium*, the extract or the composition being intended for reducing or even inhibiting the glycation of proteins, particularly the glycation of the proteins of the skin and/or of its annexes.

The expression active ingredient is understood to mean any molecule or extract capable of modifying or of modulating the functioning of at least one given biological system.

Most particularly, the subject of the invention is the use, in a composition or for the preparation of a composition, of an effective quantity of at least one extract of at least one plant of the genus *Vaccinium*, the extract or the composition being intended for reducing or even inhibiting the glycation of the proteins of the dermis, such as for example collagen, and/or of the nails and/or of the hair, such as for example keratins.

Thus, the subject of the invention is the use, in a composition or for the preparation of a composition, of an effective quantity of at least one extract of at least one plant of the genus *Vaccinium*, the extract or the composition being intended for treating, preventively and/or curatively, the signs of ageing of the skin or of its annexes linked to glycation.

The genus *Vaccinium* comprises more than 450 species, among which there may be mentioned the species *Vaccinium myrtillus*, *Vaccinium angustifollium*, *Vaccinium arboreum*, *Vaccinium arctostaphylos*, *Vaccinium caespitosum*, *Vaccinium corymbosum*, *Vaccinium hirsutum*, *Vaccinium macrocarpum*, *Vaccinium ovatum*, *Vaccinium oxycoccos*, *Vaccinium stamineum*, *Vaccinium uliginosum*, *Vaccinium urceolatum* and *Vaccinium vitis-idaea*.

Thus, the extract of a plant of the genus *Vaccinium* of the invention is an extract prepared from material derived from at least one plant belonging to a species chosen from the species *Vaccinium myrtillus*, *Vaccinium angustifollium*, *Vaccinium arboreum*, *Vaccinium arctostaphylos*, *Vaccinium caespitosum*, *Vaccinium corymbosum*, *Vaccinium hirsutum*, *Vaccinium macrocarpum*, *Vaccinium ovatum*, *Vaccinium oxycoccos*, *Vaccinium stamineum*, *Vaccinium uliginosum*, *Vaccinium urceolatum* and *Vaccinium vitis-idaea*.

Preferably, according to the invention, the plant belongs to the species *Vaccinium angustifollium*.

The extract of at least one plant of the genus *Vaccinium* may be any extract prepared from any plant material derived from at least one plant of the genus *Vaccinium*.

Thus, the extract of at least one plant of the genus *Vaccinium* used according to the invention may be obtained from plant material derived from a whole plant or from a plant portion such as the leaves, the stems, the flowers, the petals, the fruit, the roots or dedifferentiated cells.

The expression dedifferentiated plant cells is understood to mean any plant cell not having any of the characteristics of a particular specialization and which is capable of living by itself and not in dependence on other cells. These undifferentiated plant cells are potentially capable, under the effect of induction, of any differentiation in accordance with their genome.

Depending on the method of culture chosen, and in particular depending on the culture medium chosen, it is possible to obtain, from the same explant, dedifferentiated plant cells having different characteristics.

Preferably, the fruits are used according to the invention.

The extract of at least one plant of the genus *Vaccinium* may be any extract prepared from any plant material derived from at least one plant of the genus *Vaccinium* cultured in vivo or derived from in vitro culture.

The expression in vivo culture is understood to mean any conventional type culture, that is to say in soil in the open air or in a greenhouse, or soil-free culture. The expression in vitro is understood to mean all the techniques known to a person skilled in the art which make it possible artificially to obtain a plant or a portion of a plant. The selection pressure imposed by the physicochemical conditions during the growth of the plant cells in vitro makes it possible to obtain a standardized plant material which is available throughout the year, unlike the plants cultured in vivo.

Preferably, a plant derived from in vivo culture is used according to the invention.

Any method of extraction known to a person skilled in the art may be used to prepare the extract contained in the composition according to the invention.

There may be mentioned in particular aqueous extracts, alcoholic extracts or extracts using an organic solvent.

The expression aqueous solvent is understood to mean any solvent which completely or partly consists of water. There may thus be mentioned water itself, aqueous-alcoholic solvents in any proportion or alternatively solvents consisting of water and a compound such as propylene glycol in any proportion.

Ethanol may be cited in particular among the alcoholic solvents.

It is also possible to use an extract prepared by the method described in French patent application No. 95-02379 filed by the applicant.

Thus, in a first step, the plant material is ground in an aqueous solution at low temperature, in a second step, the particles in suspension are removed from the aqueous solution derived from the first step, and in a third step, the aqueous solution derived from the second step is sterilized. This aqueous solution corresponds to the extract.

Moreover, the first step may be advantageously replaced by a simple operation of freezing the plant tissues (for example at −20° C.),followed by an aqueous extraction repeating the second and third steps described above.

Regardless of the mode of preparation used according to the invention, subsequent steps intended to promote preservation and/or stabilization may be added, without as a result, modifying the actual nature of the extract. Thus, for example, the extract obtained may be freeze-dried by any conventional freeze-drying method. A powder is thus obtained which may be used directly or alternatively mixed in an appropriate solvent before use.

Preferably, according to the invention, there is used an aqueous extract and still more preferably an extract made with a solvent composed of water and propylene glycol, such as for example Herbasol® sold by the company COSMETOCHEM's.

According to the invention, the extracts of at least one plant of the genus *Vaccinium* may be used alone or in the form of mixtures of any type and may be of natural or synthetic origin.

In particular, the extract of at least one plant of the genus *Vaccinium* or the composition containing it is used according to the invention for topical application to the skin and/or the nails and/or the hair.

The quantity of extract of at least one plant of the genus *Vaccinium* which can be used according to the invention quite obviously depends on the desired effect and should be in a quantity which is effective to reduce or even inhibit glycation.

By way of example, the quantity of extract of at least one plant of the genus *Vaccinium* which can be used according to the invention may range, for example, from 0.001% to 25% and preferably from 0.005% to 15% of the total weight of the composition.

In addition, the composition of the invention is used for a period sufficient to obtain the effects which are expected according to the invention. To give an order of magnitude, this duration may be a minimum of 3 weeks, but may also be more than 4 weeks, or even more than 8 weeks.

The composition is preferably intended for cosmetic or dermatological use, advantageously for cosmetic use.

The composition of the invention intended for topical application contains a physiologically acceptable medium, that is to say which is compatible with the skin including the scalp, its annexes, the mucous membranes and/or the eyes and may constitute in particular a cosmetic or dermatological composition.

This composition may be provided in all the galenic forms normally used in the cosmetic and dermatological fields, and it may in particular be in the form of an optionally gelled aqueous solution, an optionally two-phase dispersion of the lotion type, an emulsion obtained by dispersing a fatty phase in an aqueous phase (O/W) or conversely (W/O), or a triple emulsion (W/O/W or O/W/O) or a vesicular dispersion of the ionic and/or nonionic type. These compositions are prepared according to customary methods.

The composition of the invention may constitute, for example, a lotion, a gel, a cream or a milk, and for example a make-up-removing or cleansing lotion or milk, a shampoo or a shower gel.

The subject of the invention is also a method of cosmetic treatment for treating the signs of ageing linked to the glycation of proteins, particularly of the skin and/or the nails and/or the hair, characterized in that there is applied to the skin and/or the nails and/or the hair a cosmetic composition comprising an effective quantity of at least one extract of at least one plant of the genus *Vaccinium*, the extract or the composition being intended for inhibiting glycation.

Other characteristics and advantages of the invention will emerge more clearly from the following examples given by way of illustration and without limitation. In the text which follows or in the preceding text, the proportions are given in percent by weight, unless otherwise stated.

EXAMPLE 1

Study of the effect of an extract of *Vaccinium myrtillus* (bilberry) on glycation.

A solution of bovine serum albumin at 5 mg/ml in solution in phosphate buffered saline (PBS) is 15 incubated at 37° C. for 28 days in the presence or in the absence of D-ribose at a concentration 10 mM or of an extract of bilberry at the concentrations of 5% and 10%.

The glycation is evaluated by measuring the fluorescence (Rx) of the AGEs (range of glycation products) at $\lambda em.=440$ nm emitted by each sample after excitation at $\lambda ex.=370$ nm or alternatively at $\lambda em.=380$ nm emitted by each sample after excitation at $\lambda ex.=320$ nm (fluorescence emitted by some of the glycation products including in particular pentosidine).

The inhibition of glycation is visualized by the reduction in fluoresence compared with the sample treated with the sugar alone (R) according to the formula:

$$(R-Rx)/Rx \times 100$$

The results are in % inhibition:

|  | Extract at 5% | Extract at 10% |
|---|---|---|
| $\lambda em. = 440$ nm/$\lambda ex. = 370$ nm | 63 | 71 |
| $\lambda em. = 380$ nm/$\lambda ex. = 320$ nm | 16 | 43 |

The bilberry extract has an advantageous antiglycation effect from the concentration of 5%.

EXAMPLE 2

Examples of formulations illustrating the invention and particularly the compositions according to the invention. These compositions were obtained by simply mixing the different components.

| Composition 1: Lotion | |
|---|---|
| Herbasol ® (extract of Vaccinium myrtillus) | 1.00 |
| Antioxidant | 0.05 |
| Isopropanol | 40.00 |
| Preservative | 0.30 |
| Water | qs 100% |

| Composition 2: Treatment gel | |
|---|---|
| Herbasol ® (extract of Vaccinium myrtillus) | 4.00 |
| Hydroxypropylcellulose* | 1.00 |
| Antioxidant | 0.05 |
| Isopropanol | 40.00 |
| Preservative | 0.30 |
| Water | qs 100% |

| Composition 3: Treatment cream (oil-in-water emulsion) | |
|---|---|
| Herbasol ® (extract of Vaccinium myrtillus) | 5.00 |
| Glyceryl stearate | 2.00 |
| Polysorbate 60** | 1.00 |
| Stearic acid | 1.40 |
| Triethanolamine | 0.70 |
| Carbomer | 0.40 |
| Liquid fraction of shea butter | 12.00 |
| Perhydrosqualene | 12.00 |
| Antioxidant | 0.05 |
| Perfume | 0.5 |
| Preservative | 0.30 |
| Water | qs 100% |

| Composition 4: Shampoo | |
|---|---|
| Herbasol ® (extract of Vaccinium myrtillus) | 2.00 |
| Hydroxypropylcellulose* | 1.00 |
| Sodium lauryl sulphate | 12.00 |
| Perfume | 0.50 |
| Preservative | 0.30 |
| Water | qs 100% |

| Composition 5: Care cream (oil/water emulsion) | |
|---|---|
| Herbasol ® (extract of Vaccinium myrtillus) | 4.00 |
| Glyceryl stearate | 2.00 |
| Polysorbate 60** | 1.00 |
| Stearic acid | 1.40 |
| 5-n-octanoylsalicylic acid | 0.50 |
| Triethanolamine | 0.70 |

| -continued | |
|---|---|
| Carbomer | 0.40 |
| Liquid fraction of shea butter | 12.00 |
| Perhydrosqualene | 12.00 |
| Antioxidant | 0.05 |
| Perfume | 0.5 |
| Preservative | 0.30 |
| Water | qs 100% |

| Composition 6: Gel | |
|---|---|
| Herbasol ® (extract of Vaccinium myrtillus) | 10.00 |
| Hydroxypropylcellulose* | 1.00 |
| Antioxidant | 0.05 |
| Lidocaine hydrochloride | 2.00 |
| Isopropanol | 40.00 |
| Preservative | 0.30 |
| Water | qs 100% |

| Composition 7: Treatment cream (oil-in-water emulsion) | |
|---|---|
| Herbasol ® (extract of Vaccinium myrtillus) | 20.00 |
| Glyceryl stearate | 2.00 |
| Polysorbate 60** | 1.00 |
| Stearic acid | 1.40 |
| Glycyrrhetinic acid | 2.00 |
| Triethanolamine | 0.70 |
| Carbomer | 0.40 |
| Liquid fraction of shea butter | 12.00 |
| Sunflower oil | 10.00 |
| Antioxidant | 0.05 |
| Perfume | 0.5 |
| Preservative | 0.30 |
| Water | qs 100% |

| Composition 8: Gel | |
|---|---|
| Herbasol ® (extract of Vaccinium myrtillus) | 8.00 |
| All-trans-retinoic acid | 0.05 |
| Hydroxypropylcellulose* | 1.00 |
| Antioxidant | 0.05 |
| Isopropanol | 40.00 |
| Preservative | 0.30 |
| Water | qs 100% |

*Klucel H ® sold by the company Hercules
**Tween 60 ® sold by the company ICI

The invention claimed is:

1. Method of cosmetic or dermatological treatment for treating an individual having the signs of ageing caused by glycation of proteins of the skin and/or the nails and/or the hair, comprising applying to the skin and/or the nails and/or the hair of said individual in need thereof, a cosmetic or dermatalogical composition comprising an effective quantity ranging from 1% to 20% of the total weight of the composition of at least one extract of at least one plant of the genus *Vaccinium*, the quantity of the extract of the composition being sufficient for inhibiting or reducing said glycation, and said plant of the genus *Vaccinium* being selected from the group consisting of *Vaccinium myrtillus, Vaccinium angustifolium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccos, Vaccinium stamineum, Vaccinium uliginosum, Vaccinium urceolatum* and *Vaccinium vitis-idaea*.

2. The method according to claim 1, wherein said extract is from the species *Vaccinium myrtillus*.

3. The method according to claim 1, wherein said cosmetic or dermatological composition is topically administered in the form of a lotion, gel, cream, milk or shampoo.

4. The method according to claim 1, wherein said plant extract is derived from the fruit of the plant.

5. A method for treating an individual having signs of aging caused by glycation of proteins which comprises administering to said individual a composition comprising an effective amount ranging from 1 to 20 by weight of the composition, of an abstract of at least one plant of the genus *Vaccinium* in an amount effective to substantially inhibit or reduce glycation of proteins in said individual, said plant of the genus *Vaccinium* being selected from the group consisting of *Vaccinium myrtillus, Vaccinium angustifolium, Vaccinium arboreum, Vaccinium arctostaphylos, Vaccinium caespitosum, Vaccinium corymbosum, Vaccinium hirsutum, Vaccinium macrocarpum, Vaccinium ovatum, Vaccinium oxycoccos, Vaccinium stamineum, Vaccinium uliginosum, Vaccinium urceolatum* and *Vaccinium vitis-idaea*.

6. The method according to claim 5, wherein the proteins are proteins of the skin and/or the nails and/or the hair.

7. The method according to claim 6, wherein the proteins of the skin are proteins of the dermis.

8. The method according to claim 7, wherein the protein comprises collagen.

9. The method according to claim 6, wherein the proteins of the nails and/or the hair are keratins.

10. The method according to claim 5, wherein glycation reduction or inhibition is evident after treatment for a minimum of 3 weeks.

11. The method according to claim 5, wherein the signs of aging caused by glycation of proteins include lack of tonicity of the skin, thinning of the dermis, reduction in heat denaturation, increase in resistance to enzymatic digestion, increase in intermolecular bridgings and difficulty in solubilizing and degrading and renewing collagen.

12. The method according to claim 5, wherein said extract is from the species *Vaccinium myrtillus*.

13. The method according to claim 5, wherein said plant extract is derived from the fruit of the plant.

14. The method according to claim 5, wherein said extract is topically administered in the form of a lotion, gel, cream, milk or shampoo.

15. The method according to claim 5, wherein the sign of aging comprises a lack of skin tone.

16. The method according to claim 5, wherein the sign of aging comprises thinned skin.

* * * * *